United States Patent
Milavetz

[11] Patent Number: 6,083,215
[45] Date of Patent: Jul. 4, 2000

[54] METHOD AND APPARATUS FOR ANTEGRADE CORONARY PERFUSION

[76] Inventor: James J. Milavetz, 3539 Cedar Lake Ave., Minneapolis, Minn. 55416

[21] Appl. No.: 08/503,387

[22] Filed: Jul. 17, 1995

[51] Int. Cl.$^7$ .................................................. A61M 31/00
[52] U.S. Cl. ........................... 604/509; 604/4; 604/264; 604/508; 128/898
[58] Field of Search ................... 604/4, 49, 53, 604/96, 51, 52, 97, 98, 99, 101, 102, 103; 600/16, 17, 18; 606/194; 128/898

[56] References Cited

U.S. PATENT DOCUMENTS

| | | | |
|---|---|---|---|
| 3,592,184 | 7/1971 | Watkins et al. | 128/1 R |
| 3,720,200 | 3/1973 | Laird | 128/1 D |
| 4,196,729 | 4/1980 | Nathan et al. | 128/214 E |
| 4,345,594 | 8/1982 | Bisera et al. | 128/214 F |
| 4,456,000 | 6/1984 | Schjeldahl et al. | 128/1 D |
| 4,459,977 | 7/1984 | Pizon et al. | 128/1 D |
| 4,493,697 | 1/1985 | Krause et al. | 604/50 |
| 4,531,936 | 7/1985 | Gordon | 604/49 |
| 4,569,332 | 2/1986 | Schiff et al. | 128/1 D |
| 4,592,340 | 6/1986 | Boyles | 128/1 D |
| 4,648,384 | 3/1987 | Schmukler | 604/4 |
| 4,697,574 | 10/1987 | Karcher et al. | 128/1 D |
| 4,753,221 | 6/1988 | Kensey et al. | 128/1 D |
| 4,804,358 | 2/1989 | Karcher et al. | 600/17 |
| 4,865,581 | 9/1989 | Lundquist et al. | 600/18 |
| 4,884,573 | 12/1989 | Wijay et al. | 128/344 |
| 4,921,483 | 5/1990 | Wijay et al. | 604/96 |
| 5,021,045 | 6/1991 | Buckberg et al. | 604/53 |
| 5,024,668 | 6/1991 | Peters et al. | 606/194 |
| 5,066,282 | 11/1991 | Wijay et al. | 604/152 |
| 5,135,467 | 8/1992 | Citron | 600/16 |
| 5,158,540 | 10/1992 | Wijay et al. | 604/43 |
| 5,195,942 | 3/1993 | Weil et al. | 600/18 |
| 5,295,959 | 3/1994 | Gurbel et al. | 604/96 |
| 5,300,113 | 4/1994 | Arpesella et al. | 623/3 |
| 5,324,260 | 6/1994 | O'Neill et al. | 604/96 |
| 5,330,451 | 7/1994 | Gabbay | 604/284 |
| 5,383,854 | 1/1995 | Safar et al. | 604/98 |
| 5,429,144 | 7/1995 | Wilk | 128/898 |
| 5,486,159 | 1/1996 | Mahurkar | 604/4 |
| 5,533,957 | 7/1996 | Aldea | 600/16 |
| 5,584,803 | 12/1996 | Stevens et al. | 604/4 |
| 5,597,377 | 1/1997 | Aldea | 600/16 |
| 5,678,570 | 10/1997 | Manning | 128/897 |

Primary Examiner—Mark O. Polutta
Assistant Examiner—William Noggle
Attorney, Agent, or Firm—Larkin, Hoffman, Daly & Lindgren, Ltd.

[57] ABSTRACT

A multi-lumen catheter and method for providing antegrade perfusion to an ischemic region of the myocardium of a patient induced by a coronary or vascular deficiency, including a restriction or obstruction in the vessel such as an athesclerotic lesion or stenosis, embolism, thrombosis, vessel spasm, aneurysm, or the like. The distal tip of the catheter is introduced by a conventional percutaneous transluminal procedure via the femoral or brachial artery and advanced through the vascular system to a position closely proximate to the ischemic region. A volume of oxygenated blood is withdrawn into a lumen of the catheter from a position remote to the deficiency, circulated through a pump assembly and filter, and expelled from the distal tip of the catheter to increase the supply of oxygenated blood reaching the ischemic region. The catheter may be advanced directly to or past the deficiency within the same arterial vessel, or the volume of oxygenated blood may be supplied to the ischemic region via a collateral arterial pathway. An inflatable balloon may be used to anchor the distal tip of the catheter in a selected position and to block retrograde perfusion, and a pressure transducer may monitor pressure levels within the vessel and be used to responsively control the pressure at which the oxygenated blood is expelled.

19 Claims, 5 Drawing Sheets

METHOD AND APPARATUS FOR ANTEGRADE CORONARY PERFUSION

BACKGROUND OF THE INVENTION

1. Field of the Invention

This invention relates generally to percutaneous transluminal catheters used for the clinical treatment of a coronary and vascular deficiency, and particularly to a catheter for the antegrade perfusion of an ischemic region of the myocardium induced by a coronary or vascular deficiency.

2. Prior Art

The treatment of coronary or vascular defects and diseases represents a significant portion of the current expenditure in critical care time and resources, however both the short- and long-term success or survival rates among afflicted patients remains surprisingly far below the expectations of most practitioners.

Accepted treatments encompass a wide spectrum of modalities depending upon the type and severity of the coronary deficiency, from heart transplants, bypass surgery, intra-aortic balloon pumping, angioplasty, atherectomy, and thrombolytic drug treatment. These procedures each have incumbent risks and limitations, and their use is frequently dictated by the circumstances of the patient's immediate acute condition, and the available time, equipment, and personnel that can be utilized. Somewhat unexpectedly, the current research and literature suggest that relative success rates for less invasive or complicated procedures may not be significantly different than expensive and complex options such as bypass surgery.

One option that is the subject of current research is perfusing blood from a femoral artery through the distal tip of an angioplasty catheter during the angioplasty procedure. The goal is to minimize the deleterious effects of further blocking a stenosed arterial vessel with the inflated angiolasty balloon, usually for the 3 to 10 minute inflation period required to perform the compressive angioplasty procedure.

Another option is perfusing blood to a proximal site within the aorta or myocardium at an elevated pressure to induce increased circulation in the secondary or tertiary collaterals directly surrounding the ischemic region. This procedure relies on the presence and degree of the patient's existing collateral circulation within substantially the same collateral bed as the "culprit" or afflicted arterial vessel.

The present invention is directed to the principle that the most dramatic and life-threatening effects of a coronary or vascular deficiency may be minimized significantly by providing oxygenated blood to ischemic regions of the myocardium (or other organs or muscle tissue) induced by the deficiency. Such deficiencies can include an athesclerotic lesion or stenosis, thrombus, embolism, vessel spasm, or other types of a restriction in or obstruction of an arterial vessel.

One representative example is the pathogenesis of cardiogenic shock complicating myocardial infarction, wherein the obstruction of a major coronary artery leads to myocardial ischemia—thereby triggering a downward spiral of reduced contractile mass leading to decreased left ventricular function and a corresponding decline in arterial pressure and reduced coronary perfusion, prompting a further reduction in contractile mass, decreasing left ventricular function, declining arterial pressure, and diminishing coronary perfusion—eventually leading to the death of the patient unless the spiral is interrupted and reversed by homeostatic mechanisms or an external therapeutic force.

Cardiogenic shock may also cause the death of a patient who initially survives a moderate or less severe episode of arterial obstruction but then progresses to experience a recurrent arterial obstruction or plural obstructions. This may occur despite aggressive intervention such as coronary angioplasty or bypass surgery. The degree to which cardiogenic shock affects the viability of any eventual therapy depends on the rate of the downward spiral, the length of time which elapses, and the effectiveness of the measures employed to reverse the cardiogenic shock prior to or during the restoration of normal circulation. Even if the therapy proves successful in the short-term, the chances for long-term survival can be significantly diminished (and permanency of any deleterious effects of the infarction significantly magnified) by the progress of cardiogenic shock during the lapse in time between the initial onset of the arterial deficiency and the eventual application of a comprehensive treatment modality.

It has been shown in the literature that survival following myocardial infarction is directly related to the degree of remaining viable myocardium. For example, patients surviving myocardial infarction with severely decreased heart function have greater than 70% mortality by 5 years. By comparison, patients who survive myocardial infarction with minimal damage to the heart may have an 80–90% chance of 5 year survival. Consequently, even intermediate success in lowering the extent of infarction damage can have a dramatic impact on patient survival rates, the extent of interventional and long-term care required for a patient, and the quality of life experienced by that patient.

BRIEF SUMMARY OF THE INVENTION

It is therefore one object of this invention to design a method and apparatus for providing antegrade perfusion over a relatively extended period of time to an ischemic region of the myocardium (or other organ or muscle tissue) induced by a coronary or vascular deficiency.

It is another object of this invention to design the method and apparatus to provide a supply of oxygenated blood to the ischemic region directly via the arterial pathway containing the deficiency, or indirectly via a collateral arterial pathway that includes a collateral bed that is closely proximate to the ischemic region but arises from a non-culprit or non-hemodynamically significantly affected arterial vessel.

It is a further object of this invention to design the method and apparatus to be used virtually immediately upon the discovery of an arterial deficiency—namely, a coronary obstruction or restriction leading to an ischemic region of the myocardium—to prevent or delay the onset of cardiogenic shock or minimize its deleterious effects until such time that a comprehensive therapy to restore normal circulation can be employed.

It is a related object of this invention to design the above method and apparatus to such that medical personnel having a wider spectrum of training and experience may select and initiate the procedure with minimal risk to the patient even absent extensive diagnostic screening, and without requiring the utilization of significant time, equipment, manpower, or facilities.

Briefly described, the apparatus of this invention comprises a multi-lumen catheter and a method for providing antegrade perfusion to an ischemic region of the myocardium of a patient resulting from a coronary or vascular deficiency, including a restriction or obstruction in the vessel such as an atherosclerotic lesion or stenosis, embolism, thrombosis, vessel spasm, aneurysm, or the like. The distal tip of the catheter is introduced by a conventional percutaneous transluminal procedure via the femoral or brachial artery and advanced through the vascular system to a position closely proximate to the ischemic region. A volume of oxygenated blood is withdrawn into a lumen of the catheter from a position remote to the deficiency, circulated through a pump assembly and filter, and expelled from the distal tip of the catheter to increase the supply of oxygenated blood reaching the ischemic region. The catheter may be advanced directly to or past the deficiency within the same arterial vessel, or the volume of oxygenated blood may be supplied to the ischemic region via a collateral arterial pathway. An inflatable balloon may be used to anchor the distal tip of the catheter is a selected position and to block retrograde perfusion, and a pressure transducer may monitor pressure levels within the vessel and be used to responsively control the pressure at which the oxygenated blood is expelled.

DESCRIPTION OF THE PREFERRED EMBODIMENTS

The antegrade coronary perfusion catheter of this invention is shown in FIGS. 1–10 and referenced generally therein by the numeral 10.

Referring particularly to FIGS. 1–8, the catheter 10 is fabricated using techniques and materials generally consistent with the construction of percutaneous transluminal coronary angiography (PTA) and angioplasty (PTCA) catheters, and the knowledge of those of ordinary skill in such art and the future improvements and refinements to such catheters may be utilized as appropriate in the antegrade coronary perfusion catheter 10 of this invention.

The catheter 10 described herein is of the dual lumen or side-by-side lumen type, whereas it may be readily appreciated that alternate embodiments such as a coaxial lumen type may be employed as appropriate given the components, features, and operating characteristics desired.

The catheter 10 includes a body portion 12 having an overall length on the order of 150–200 cm, and further having a distal end 14 and a proximal end 16. The proximal end 16 of the catheter 10 is adapted to be operatively connected to a pump assembly 18 as described subsequently.

The body 12 of the catheter 10 is molded from a synthetic material such as biocompatible silicone and defines a primary or central lumen 20, a secondary or radial lumen 22, a third or inflation lumen 24, and a conduit lumen 26. The central lumen 20 extends substantially completely between the distal end 14 and proximal end 16 of the body 12 of the catheter 10.

Figures 1, 2, 3:
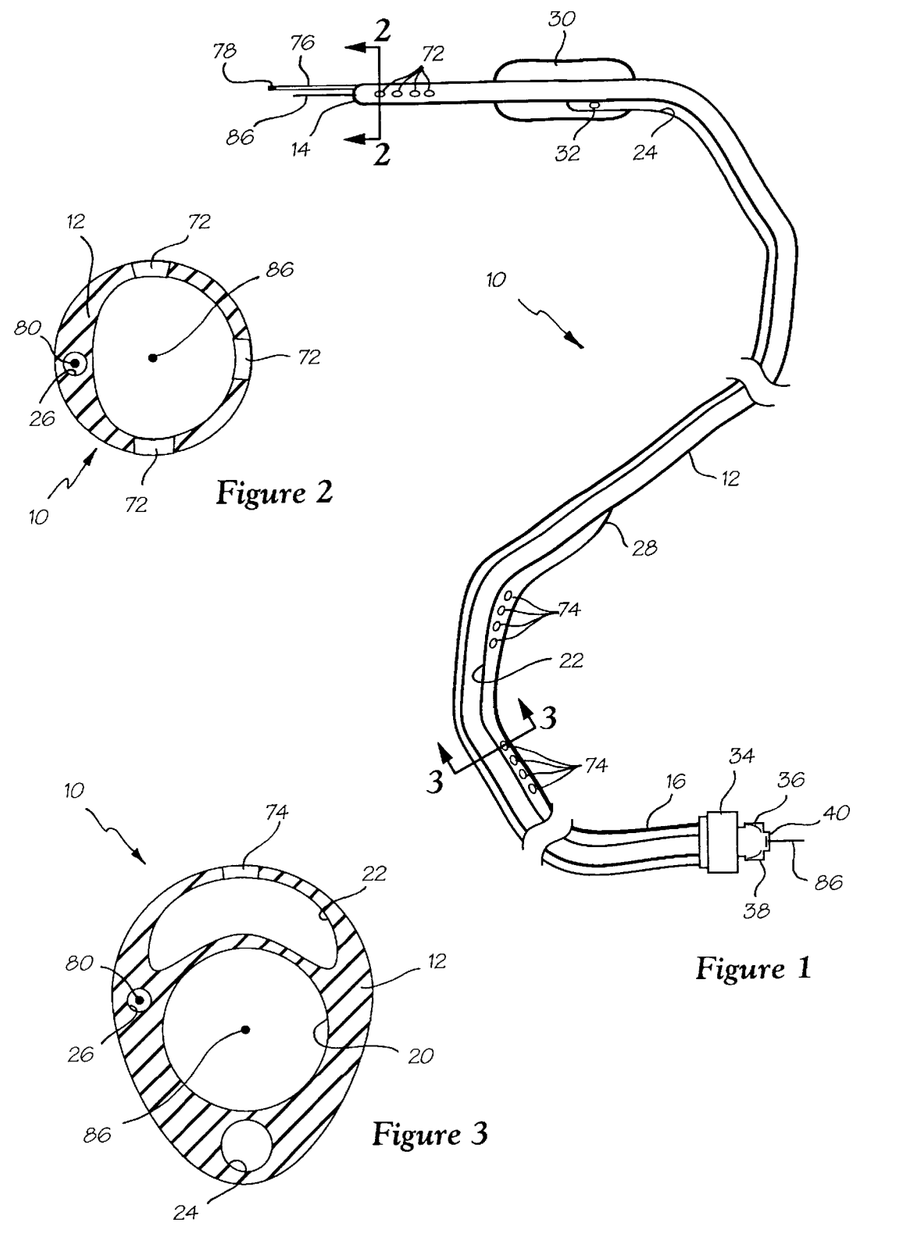
FIG. 1 is a partially broken away diagrammatic view of one embodiment of the coronary perfusion catheter of this invention.
FIG. 2 is a cross section view of the coronary perfusion catheter of FIG. 1 taken through line 2—2 of FIG. 1.
FIG. 3 is a cross section view of the coronary perfusion catheter of FIG. 1 taken through line 3—3 of FIG. 1.

In the embodiment of the catheter 10 shown in FIGS. 1–3, the secondary lumen 22 extends parallel with the central lumen from the proximal end 16 to a location along the body 12 of the catheter 10 disposed substantially remote to the distal end 14, that secondary lumen 22 defining a closed or sealed terminal end 28.

Figures 4, 5, 6:
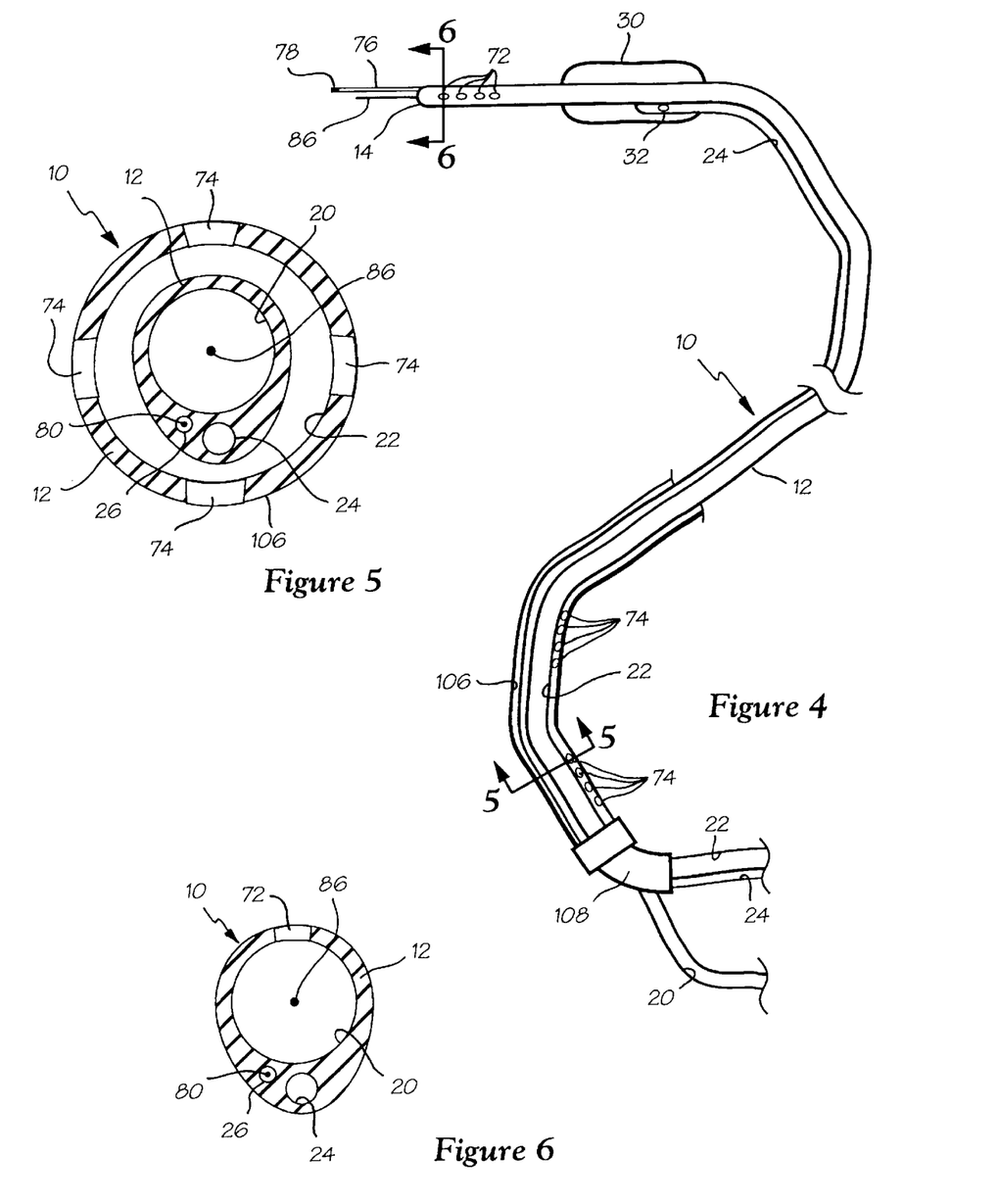
FIG. 4 is a partially broken away diagrammatic view of an alternate embodiment of the coronary perfusion catheter of this invention including a guide catheter.
FIG. 5 is a cross section view of the coronary perfusion catheter of FIG. 4 taken through line 5—5 of FIG. 4.
FIG. 6 is a cross section view of the coronary perfusion catheter of FIG. 4 taken through line 6—6 of FIG. 4.

The catheter 10 of FIGS. 4–6 may be used with a separate guide catheter 106, however this will normally increase the required profile of the catheter assembly. The guide catheter 106 will further need to define apertures in the vicinity of the inlet apertures 74 of the catheter 10 to permit ingress of oxygenated blood from a position remote to the coronary deficiency.

Consequently, in the embodiment shown in FIGS. 4–6 in which a guide catheter 106 is utilized and envelopes the catheter 10, the secondary lumen 22 is defined by that guide catheter 106 with the guide catheter 106 further defining the inlet apertures 74 at a position remote to the distal tip 14 of the catheter 10. The guide catheter 10 may be a separate component that is operatively connected to and therefore becomes a part of the catheter body 12, or it may be formed integrally with the remainder of the catheter body 12 with a portion defining the central lumen 20 being inserted through an port 108 and within the guide catheter 106 as shown in FIG. 4.

In either embodiment, the catheter 10 may include an inflatable balloon 30 fabricated in a manner similar to inflatable balloons conventionally utilized for compressive angioplasty or distal fixation of a perfusion catheter, the inflatable balloon 30 being disposed adjacent to but spaced a predetermined distance apart from the distal end 14 of the catheter 10, the interior region of the inflatable balloon 30 fluidly communicating with the inflation lumen 24 through at least one an orifice 32, the inflation lumen terminating within the interior of the inflatable balloon 30.

Referring again to the embodiment shown in FIGS. 1–3, the catheter 10 is equipped with a connector 34 having a plurality of ports 36–40 disposed to fluidly communicate with the primary lumen 20, secondary lumen 22, and inflation lumen 24. The connector 34 engages a mating connector 42 which provides corresponding fluid communication with tubing extending to an pump inlet 44, a pump outlet 46, and a Harkley-type syringe connector 48. A filter 50 to remove air or other gas bubbles is disposed along the pump outlet 46. The syringe connector 48 provides a one-way fluid-tight valve that may be engagingly and releasably connected to a pressure metered syringe 52 for injecting a fluid substance (an inert gas or a liquid such as diluted radiographic contrast dye or physiological saline) through the inflation lumen 24 to inflate the inflatable balloon 30.

Figures 7, 8:
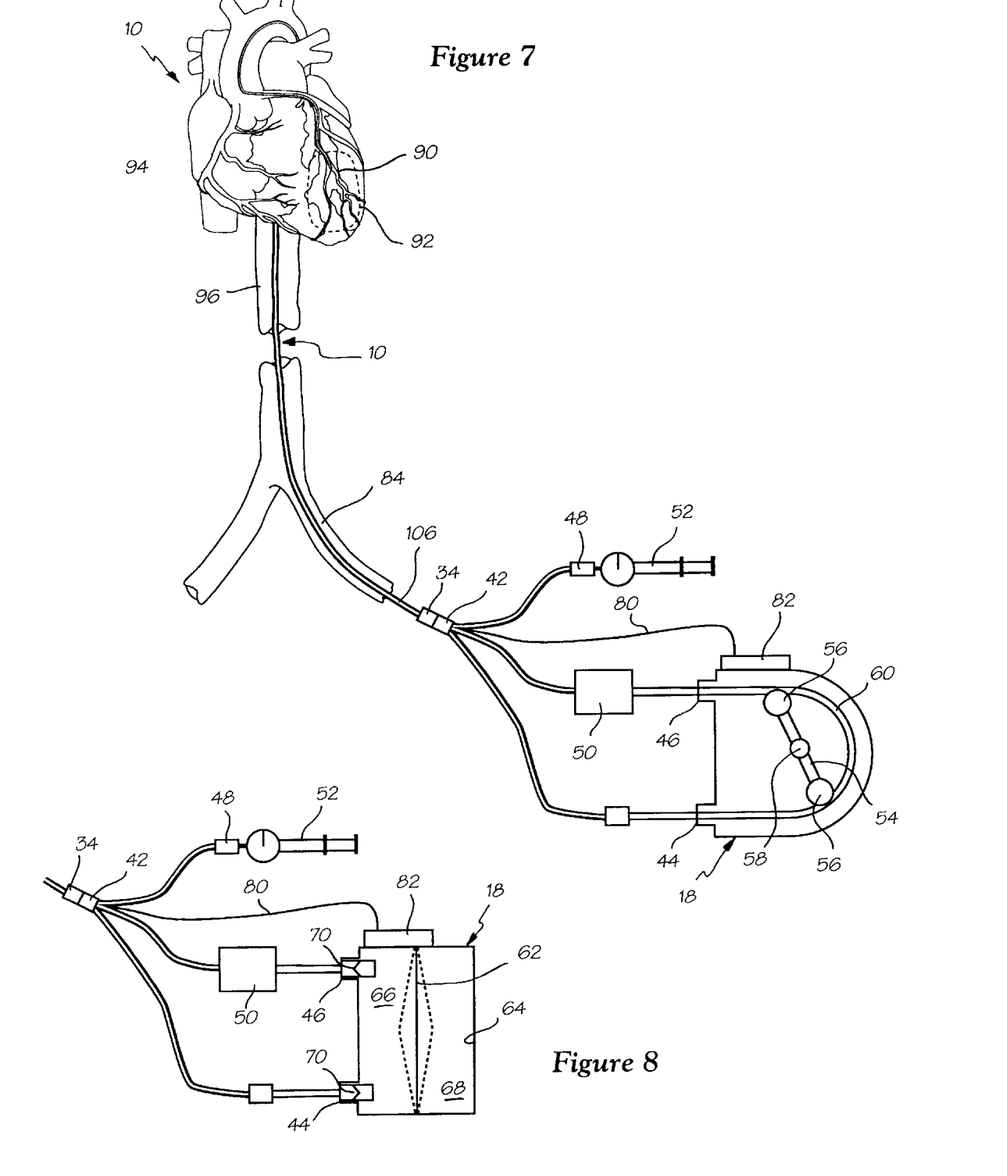
FIG. 7 is a diagrammatic view of the coronary perfusion catheter of this invention operatively connected to a peristaltic pump, with the distal tip of the catheter inserted within the left anterior descending artery of the heart.
FIG. 8 is a broken away diagrammatic view of the proximal end of the coronary perfusion catheter of this invention operatively connected to an oscillating membrane pump.

Referring particularly to FIG. 7, the pump assembly 18 is a peristaltic type pump in which a rotor 54 having a plurality of compression rollers 56 rotate about a hub 58 in a predetermined direction, each roller 56 compressing a section of flexible Tygon or similar tubing 60 to force the circulation of fluid through the pump assembly 18 from the pump inlet 44 to the pump outlet 46. Since the direction of rotation of the rotor 54 may be reversed in a peristaltic type pump to reverse the flow of the fluid between the pump outlet 46 and the pump inlet 44, a mechanical or electronic safety to prevent inadvertent reversal of the pump direction may be employed.

Alternately, as shown in FIG. 8 the pump assembly 18 is an oscillating membrane type pump in which a flexible or movable membrane 62 is disposed within a closed chamber 64, with the fluid to be pumped being contained on a first side 66 of the membrane 62. The membrane is driven through reciprocal oscillations by mechanical force exerted on the membrane 62, or by alternating a pneumatic pressure and vacuum applied to the opposing side 68 of the membrane 62. A pair of unidirectional check valves 70 disposed on the pump inlet 44 and the pump outlet 46 regulate the flow of fluid through the closed chamber 64 of the pump assembly 18 in only one predetermined direction of flow. A piston type pump of the type known to the prior art (not shown) may similarly be utilized, and may include an apparatus to convert pulsatile into semi-continuous flow.

The body 12 of the catheter 10 defines a plurality of outlet apertures 72 disposed in a predetermined array or pattern around the circumference or at the tip of the catheter 10 proximate to the distal end 14, the outlet apertures 72 extending through the body 12 of the catheter 10 and fluidly communicating with the primary lumen 20. Similarly, the catheter 10 defines a plurality of inlet apertures 74 disposed in a predetermined array or pattern along the body 12 of the catheter 10 adjacent to the terminal end 28 or spaced at a predetermined position or intervals between the proximal end 16 and the terminal end 28, the inlet apertures 74 extending through the body 12 of the catheter 10 and fluidly communicating with the secondary lumen 22.

For applications where distal pressure measurement is desired, the distal end 14 of the body 12 of the catheter 10 is provided with a thin tubular extension 76 to which a pressure transducer 78 such as a Millar transducer is mounted, the pressure transducer 78 being disposed a predetermined distance on the order of 2 cm from the distal tip 14 of the primary lumen 20. Electrical leads 80 for transmitting the signal produced by the pressure transducer 78 extend through the tubular extension 76 and through the conduit lumen 26, and are electrically connected to a signal processing and control circuit 82 mounted on and operatively connected to the rate control of the pump assembly 18. Alternately, the conduit lumen 26 may not have an electrical transducer lead but will save as a fluid filled conduit to monitor distal pressure.

It may therefore be appreciated that the catheter 10 and pump assembly 18 thereby form an enclosed circuitous path for a fluid such as the patient's blood extending from the inlet apertures 74, through the secondary lumen 22 toward the proximal end 16 of the catheter 10, through the connectors 34, 42, into the pump assembly 18 through the pump inlet 44 and out through the filter 50, through the connectors 42, 34, and through the primary lumen 20 to the outlet ports 72 at the distal end 14 of the catheter 10.

The inflation fluid may be selectively injected from the syringe 52 through the syringe connector 48, the intermediate tubing and mating connectors 42, 34, inflation lumen 24, orifice 32, and into the interior of the inflatable balloon 30 to inflate the inflatable balloon 30 to the desired radial diameter or radial pressure.

In operation, the catheter 10 is inserted into the arterial branch of the vascular or circulatory system 84 of the patient such as the femoral, iliac, or brachial artery using a conventional Seldinger percutaneous transluminal procedure. In brief, a standard arterial sheath is placed in either the femoral or brachial artery using standard techniques. A guide wire 86 is then progressively advanced until its distal tip is disposed at the position which the cardiologist or other practitioner desires to place the catheter 10. A guide catheter 106 is placed over the guide wire 86 and advanced along the guide wire 86 into position, and guide wire 86 is then withdrawn. A second steerable intracoronary guide wire 86 is then inserted within the catheter 10, and the catheter 10 and guide wire 86 are advanced to the distal end of the guide catheter 106. The guide wire 86 is then advanced to the desired location within the coronary arteries, and the catheter 10 is advanced over the guide wire 86 and through the guide catheter 106 to the desired position.

The catheter 10 is passed over the guide wire 86 with the guide wire 86 being received within the central lumen 20 of the catheter 10 and extending distally through a guide wire aperture at the distal tip 14 of the catheter 10.

Figure 9:
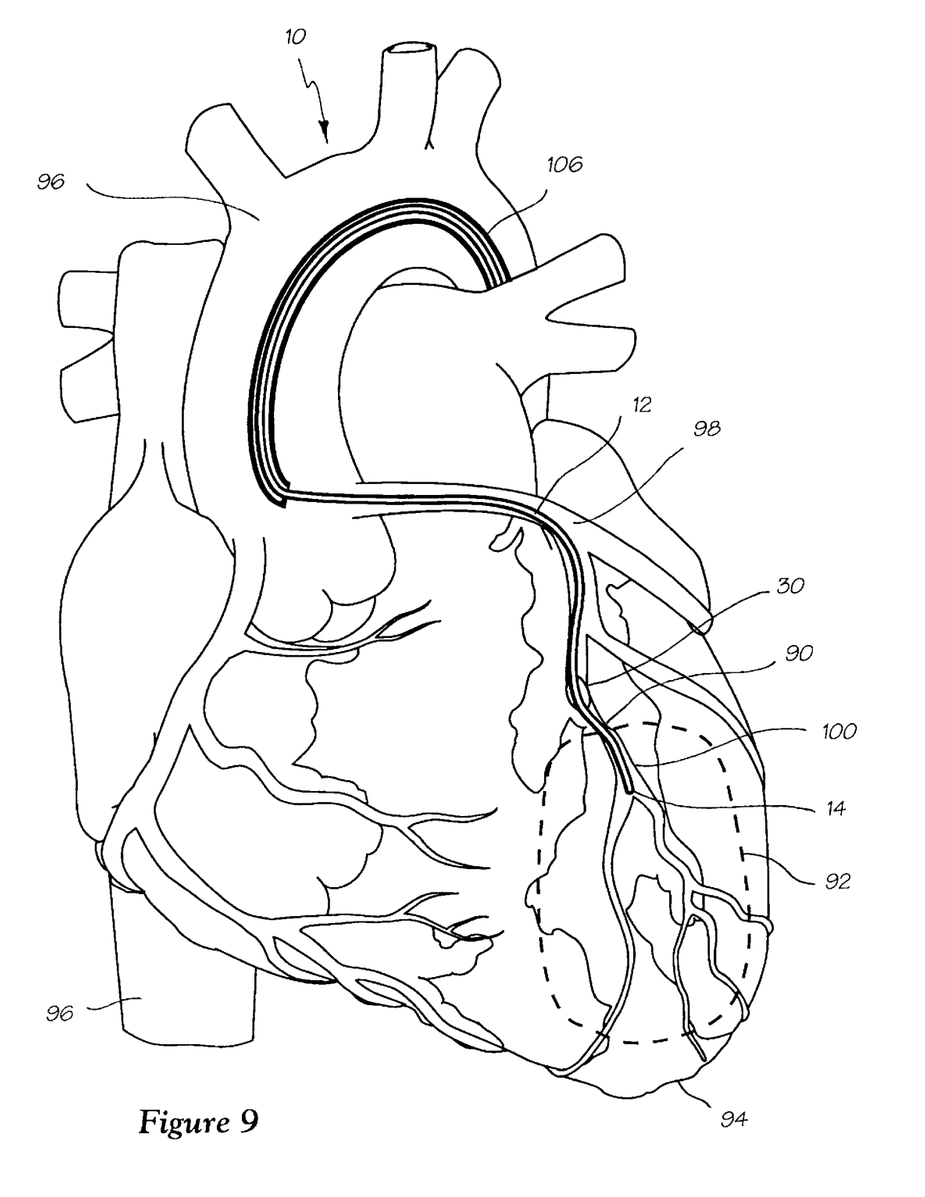
FIG. 9 is a perspective view of the heart of a patient showing the distal tip of the catheter inserted into the anterior descending branch of the left coronary artery, with a guide catheter shown partially broken away and extending only to a proximal location within the aorta.
Figure 10:
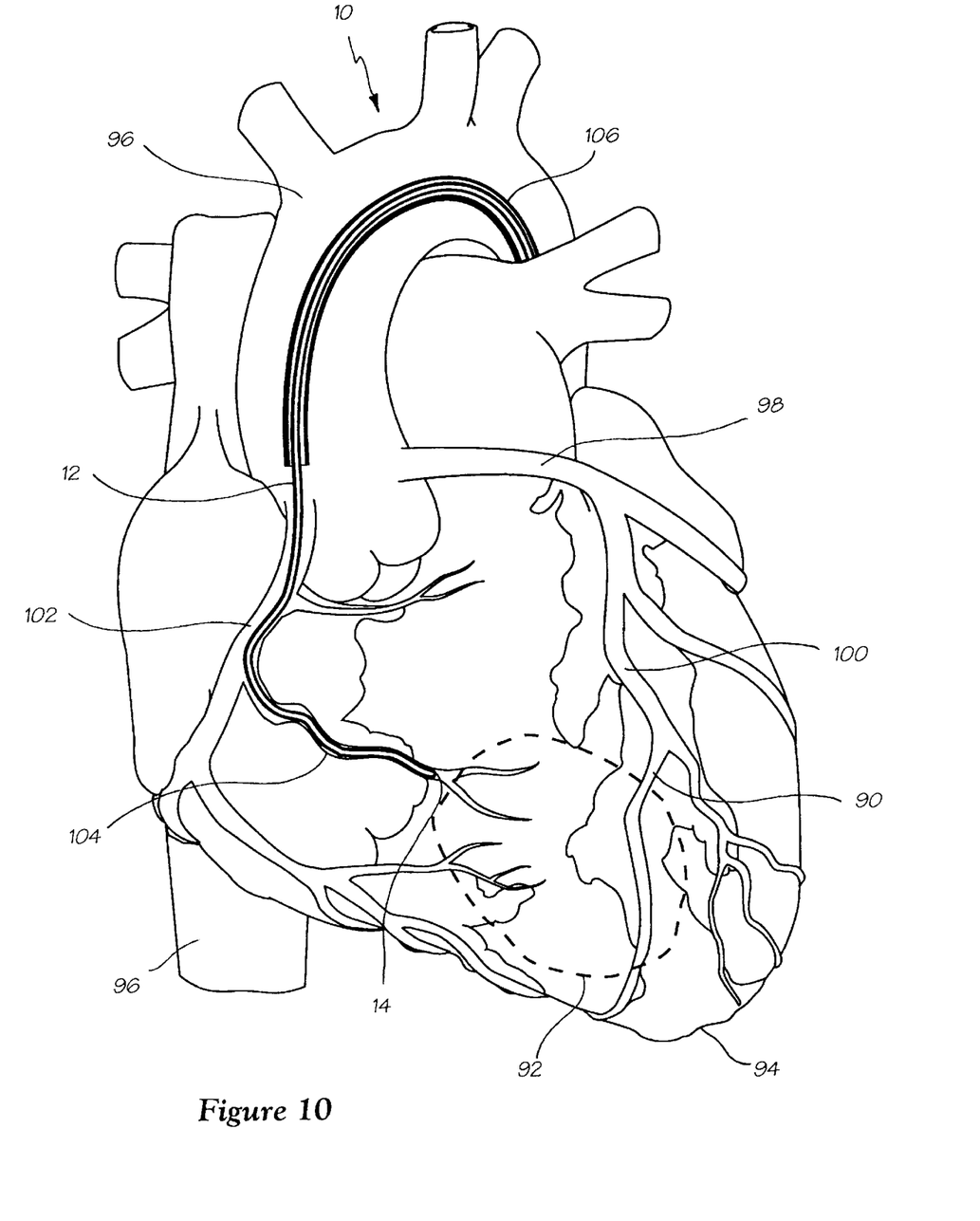
FIG. 10 is a perspective view of the heart of a patient showing the distal tip of the catheter inserted into a right diagonal branch of the right coronary artery, with a guide catheter shown partially broken away and extending only to a proximal location within the aorta.

Referring in addition to FIGS. 9 and 10, the distal end 14 of the catheter is advanced through the arterial vascular system 84 to, near, or beyond a site where a coronary or vascular deficiency 90 produces an ischemic condition reducing the normal volume of oxygenated blood and causing a region of ischemia 92 associated with that vascular deficiency 90 to occur.

Referring particularly to FIGS. 7 and 9, one representative example is shown in which the distal end 14 of the catheter 10 is inserted through the femoral artery 84, upwardly through the aorta 96 toward the patient's heart 94, and downwardly through the left anterior descending coronary artery 98 to reach a coronary deficiency 90 proximal to the diagonal branch 100 of the anterior descending coronary artery 98 producing a region of ischemia 92 encompassing a significant region of the myocardium 94 within a zone disposed generally symmetrically along the downstream portion of that left anterior descending coronary artery 98. The distal end 14 of the catheter 10 is advanced past the deficiency 90, which may be a athesclerotic lesion or stenosis, thrombosis, embolism, or similar type of restriction or obstruction of the artery 98.

Oxygenated blood is withdrawn from the arterial system 84 of the patient through the inlet apertures 74 and into the secondary lumen 22, with the inlet apertures preferably being located in a predetermined area such as the iliac artery 84 or femoral artery. The oxygenated blood is withdrawn through the secondary lumen 22, and pumped through the pumping assembly 18, filter 50, and the primary lumen 20 of the catheter 10 and expelled through the outlet apertures 72 proximate to the distal end 14 of the catheter 10, thereby providing an increased supply of oxygenated blood to the ischemic region 92 of the myocardium 94.

It may be appreciated that in some applications the distal end 14 of the catheter need not or should not traverse past the deficiency 90 in order to facilitate using the catheter 10 to increase the supply of oxygenated blood to the ischemic region 92. In such instances, the distal end 14 of the catheter may be located on the upstream side of the deficiency 90 with the increased pressure of the oxygenated blood supplied via the catheter 10 enhancing the flow through or around the deficiency 90 at pressure levels above the normal pressures within the vessel 100.

The distal end 14 of the catheter 10 may be anchored in position by inflation of the inflatable balloon 30 at a position upstream relative to the deficiency 90. The inflatable balloon 30 thereby serves to hold the catheter 10 in place over an extended period of time and to prevent retrograde perfusion in the upstream direction opposing normal circulatory pressure imparted by the function of the myocardium 94. It may be appreciated that in some applications the inflatable balloon 30 may preferably traverse past the deficiency 90 and be inflated on the downstream side of the deficiency 90 depending upon the degree of stenosis, clot burden, and the relative risks and benefits of exerting increased fluid pressure above or below the deficiency 90 within the vessel 100. (In applications involving vascular deficiencies other than coronary deficiencies, such as aneurysms, it may theoretically be preferable to block the vessel 100 with an inflatable balloon 30 disposed on both the upstream and downstream sides of the deficiency 90 to additionally reduce pressure in the area immediately adjacent to the deficiency 90.)

After perfusion via the catheter system 10 has begun, pressure readings provided by the pressure transducer 78 immediately downstream from the distal end 14 may be utilized to control the pressure and volume of oxygenated blood supplied to the ischemic region 92 through the catheter 10 and monitor pressures within the vicinity of the deficiency 90 on either the upstream or downstream side.

It may be readily appreciated that a variety of possible pressure gradients and steady or pulsed flow patterns may be devised and optimized depending upon the type of coronary deficiency 90, the relative severity of deleterious effects produced by the deficiency 90 versus the duration and nature of the perfusion treatment employed, particular physiological characteristics of the patient relevant to the type of treatment, and the results of monitoring feedback produced by the treatment. With antegrade perfusion of atherosclerotic lesions or stenoses, or similar coronary restrictions, it is anticipated that the majority of treatment modalities will approximate the normal arterial perfusion pressure or supranormal pressures as the clinical situation dictates.

Referring particularly to FIGS. 4 and 10, another representative example is shown in which the coronary deficiency 90 is similarly a restriction or obstruction within the anterior descending artery 98 creating a ischemic region 92 of the myocardium 94 disposed more medially adjacent to the path of the artery 98. The distal end 14 of the catheter 10 is similarly inserted through the femoral artery 84, upwardly toward the patient's heart 94, and through the aorta 96. In this instance, the distal end 14 of the catheter 10 is inserted along a distinct collateral arterial pathway extending downwardly through the right coronary artery 102 and traversing laterally through the right marginal branch 104 to a position proximate to the ischemic region 92. This collateral arterial pathway leads to a collateral bed including a multiplicity of secondary and tertiary collaterals (not shown) disposed in the proximity of the region of ischemia 92, but which are normally supplied with blood via non-culprit or non-hemodynamically affected arterial vessels 102, 104 that are physically separate and readily distinguishable from the stenosed vessel 98.

Oxygenated blood is withdrawn from the vascular system 84 of the patient through the inlet apertures 74 and into the secondary lumen 22 of the catheter 10, with the inlet apertures similarly being located in a predetermined area such as the aorta 96, iliac artery 84, or femoral artery. The oxygenated blood is withdrawn through the secondary lumen 22 and pumped through the pumping assembly 18, filter 50, and the primary lumen 20 of the catheter 10 and expelled through the outlet apertures 72 proximate to the distal end 14 of the catheter 10 into the right marginal branch 104, thereby providing an increased supply of oxygenated blood to the ischemic region 92 of the myocardium 94 via a collateral bed arising from the collateral arterial pathway.

It may be readily appreciated that the effectiveness of treatment utilizing collateral arterial pathways will depend upon the location of the deficiency 90, the disposition of the ischemic region 92 relative to sources of collateral circulation or access, the extent of pre-existing collateralized myocardium, and the tolerances of the collateral arterial vessels 102, 104 for supplying increased volumes of oxygenated blood to the ischemic region. In some instances, direct perfusion with the distal tip of the catheter 10 disposed closely adjacent to the region of ischemia 92 will be necessary, while in other cases it may be sufficient to perfuse oxygentaed blood at near normal or elevated pressure to a more proximal location along the collateral arterial pathway.

A wide variety of treatment modalities may be contemplated for direct deployment proximal to a critical deficiency 90 such as a stenosis or embolism, or indirect deployment utilizing a collateral circulation pathway to perfuse the area of the myocardium 92 placed at risk due to ischemia caused by the deficiency 90. Examples of treating deficiencies 90 within the left anterior descending artery 98 either directly or collaterally have been selected and described both for their representative value, and due to the prevalence of such conditions in the general population, the severity of the resultant effects, and the ineffectiveness of existing acute care strategies.

It may also be appreciated that increasing the supply of oxygenated blood to the region of ischemia 92 via the antegrade perfusion catheter 10 may include increasing flow rate, pressure, or both. Consequently, many combinations and variations in the flow rate and pressure at which the oxygenated blood is supplied may be evaluated for their immediate and long-term benefits, and selection of a suitable or optimal protocol will be dictated by the circumstances of the particular patient's clinical situation.

The methods and antegrade perfusion catheter 10 of this invention may be utilized for other modalities such as treatment of coronary deficiencies 90 affecting other portions of the myocardium 94 or circulation via other arterial pathways, as well as vascular deficiencies 90 in non-coronary sites such as arterial aneurysms or embolisms where the resulting ischemia produced ischemic regions 92 in tissue of other organs or muscles.

While the preferred embodiments of the above antegrade coronary perfusion catheter 10 have been described in detail with reference to the attached drawing Figures, it is understood that various changes and adaptations may be made in the antegrade coronary perfusion catheter 10 without departing from the spirit and scope of the appended claims.

What is claimed is:

1. A method for treating the deleterious effect of a coronary deficiency in a patient prior to and independent of initiating a necessary interventional procedure to obviate said coronary deficiency, said patient having a heart muscle and a vascular system including a first and second arterial vessel each normally conveying autologically oxygenated blood to a region of said heart muscle, said coronary deficiency associated with the first arterial vessel causing said region of said heart muscle to be ischemic, said first and second arterial vessels having collateral vessels therebetween at the ischemic region, said method comprising:

providing a catheter and a pump, said catheter having a distal end, a proximal end, and a lumen extending between and fluidly communicating with said distal end and said proximal end, said catheter being operatively connected to said pump such that the oxygenated blood may be coynveyed through said lumen from said proximal end to said distal end at a selected pressure, said catheter having an inlet aperture and an outlet aperture, said inlet aperture and said outlet aperture fluidly communicating with said lumen, said inlet aperture being disposed more closely proximate to said proximal end and said outlet aperture being disposed more closely proximate to said distal end;

inserting said catheter within the vascular system of the patient such that said distal end of said catheter is advanced into the second arterial vessel, with said inlet aperture being disposed within said vascular system in a position that is generally remote relative to the coronary deficiency and the region that is ischemic;

withdrawing a volume of the autologically oxygenated blood from the vascular system of the patient through said inlet aperture into said lumen of said catheter;

expelling that oxygenated blood from said lumen of said catheter through said outlet aperture antegradely into the second arterial vessel of the patient at said selected pressure so as to increase the supply of oxygenated blood via the collateral vessels to the region that is ischemic and diminish the deleterious effect of the coronary deficiency as a precursor to the interventional procedure to obviate the vascular deficiency; and continuing to withdraw the autologically oxygenated blood from the vascular system and expel that oxygenated blood from said catheter in a controlled manner over an extended period of time prior to and independent of initiating the interventional procedure to obviate the coronary deficiency until either the patient has stabilized sufficiently to tolerate the interventional procedure or the interventional procedure is rendered unnecessary.

2. The method of claim 1 wherein the first arterial vessel has a diameter and the coronary deficiency is a restriction in said diameter of the first arterial vessel at least partially decreasing the flow of oxygenated blood through the first arterial vessel.

3. The method of claim 2 wherein the restriction in the arterial vessel is an athesclerotic lesion.

4. The method of claim 1 wherein the coronary deficiency is an obstruction within the first arterial vessel at least partially decreasing the flow of oxygenated blood through the first arterial vessel.

5. The method of claim 4 wherein the obstruction in the arterial vessel is a thrombosis.

6. The method of claim 1 wherein the first arterial vessel is a left coronary artery and the second arterial vessel is a right coronary artery.

7. The method of claim 6 wherein the first arterial vessel arises from the left coronary circulation and the second arterial vessel arises from the right coronary circulation.

8. The method of claim 6 wherein the first arterial vessel arises from a one of either the left coronary circulation or the right coronary circulation, and the second arterial vessel arises from a remaining one of the right coronary circulation or the left coronary circulation from which the first arterial vessel does not arise.

9. The method of claim 8 wherein the catheter further includes a pressure transducer for measuring at least a pressure within the second arterial vessel distal to the outlet aperture, the flow of the oxygenated blood expelled from the lumen of the catheter through the outlet aperture into the vascular system of the patient being adjusted to obtain the selected pressure within the second arterial vessel.

10. The method of claim 1 wherein the position that is generally remoter relative to the coronary deficiency and the region that is ischemic from which the volume of oxygenated blood is withdrawn, is either an iliac or femoral artery.

11. The method of claim 1 wherein the position that is generally remote, relative to the coronary deficiency and the region that is ischemic from which the volume of oxygenated blood is withdrawn, is a brachial artery.

12. The method of claim 1 wherein increasing the supply of oxygenated blood to the region that is ischemic is accomplished by increasing the pressure within the vascular system adjacent the outlet aperture of the catheter.

13. The method of claim 1 wherein increasing the supply of oxygenated blood to the region that is ischemic is accomplished by increasing the flow rate within the vascular system adjacent the outlet aperture of the catheter.

14. A method for treating a vascular deficiency of a heart muscle in a patient, said heart muscle having a vascular system including a first and second arterial vessel normally conveying autologically oxygenated blood to a region effected by the vascular deficiency, said first arterial vessel being effected by the vascular deficiency to define an ischemic region, said first and second arterial vessels having a plurality of collateral vessels disposed therebetween at the ischemic region, said method comprising:

providing a catheter and a pump, said catheter having a distal end, a proximal end, and a lumen extending between and fluidly communicating with said distal end and said proximal end, said catheter being operatively connected to said pump such that the oxygenated blood may be conveyed through said lumen from said proximal end to said distal end at a selected pressure, said catheter having an inlet aperture and an outlet aperture, said inlet aperture and said outlet aperture fluidly communicating with said lumen, said inlet aperture being disposed more closely proximate to said proximal end and said outlet aperture being disposed more closely proximate to said distal end;

inserting said catheter into the vascular system of the heart muscle, with said inlet aperture being disposed within said vascular system in a position remote from the vascular deficiency and with said outlet aperture being disposed in the second arterial vessel;

withdrawing a volume of the autologically oxygenated blood from the vascular system of the patient from the remote position through said inlet aperture into said lumen of said catheter;

expelling said volume of the oxygenated blood from said lumen of said catheter through said outlet aperture into the second arterial vessel; and introducing autologically oxygenated blood via the collateral vessels to the ischemic region.

15. The method of claim 14, wherein the catheter further includes an inflation balloon disposed at the distal end and an inflation lumen extending between and fluidly communicating with the distal end and the proximal end, and wherein the step of inserting said catheter into the vascular system of the heart muscle additionally includes inflating the balloon to a selected pressure.

16. The method of claim 14 wherein the vascular deficiency is a lesion.

17. The method of claim 14 wherein the vascular deficiency is an aneurysm.

18. The method of claim 14 wherein the vascular deficiency is an embolism.

19. The method of claim 14 wherein the vascular deficiency is a thrombosis.

\* \* \* \* \*